United States Patent
Sealfon

(10) Patent No.: US 10,420,886 B2
(45) Date of Patent: Sep. 24, 2019

(54) MULTI-FLOW UNIVERSAL TUBING SET

(71) Applicant: Repro-Med Systems, Inc., Chester, NY (US)

(72) Inventor: Andrew L. Sealfon, Monroe, NY (US)

(*) Notice: Subject to any disclaimer, the term of this patent is extended or adjusted under 35 U.S.C. 154(b) by 346 days.

(21) Appl. No.: 14/768,189

(22) PCT Filed: Feb. 14, 2014

(86) PCT No.: PCT/US2014/016426
§ 371 (c)(1),
(2) Date: Aug. 14, 2015

(87) PCT Pub. No.: WO2014/127209
PCT Pub. Date: Aug. 21, 2014

(65) Prior Publication Data
US 2015/0374911 A1     Dec. 31, 2015

Related U.S. Application Data

(60) Provisional application No. 61/765,464, filed on Feb. 15, 2013.

(51) Int. Cl.
*A61M 5/168* (2006.01)
*A61M 5/14* (2006.01)
(Continued)

(52) U.S. Cl.
CPC ...... *A61M 5/16877* (2013.01); *A61M 5/1413* (2013.01); *A61M 5/16881* (2013.01);
(Continued)

(58) Field of Classification Search
CPC .......... A61M 5/16881; A61M 5/16827; A61M 5/1407; A61M 5/1408; A61M 5/1409;
(Continued)

(56) References Cited

U.S. PATENT DOCUMENTS 4,424,056 A * 1/1984 Urquhart ............. A61M 5/1409
                                                                  604/246
4,681,559 A * 7/1987 Hooven ............... A61M 27/006
                                                                  137/504

(Continued)

FOREIGN PATENT DOCUMENTS

| CN | 201085823 | 7/2008 |
| CN | 201139832 | 10/2008 |
| CN | 103252005 | 8/2013 |

OTHER PUBLICATIONS

International Search Report for PCT/US2014/016426, dated May 20, 2014.
(Continued)

*Primary Examiner* — Andrew M Gilbert
(74) *Attorney, Agent, or Firm* — Daniel W. Roberts; Law Offices of Daniel W. Roberts, LLC

(57) ABSTRACT

The invention provides a modular tubing system with a set of tubing segments that can be configured to provide a desired flow rate. In the modular systems described herein, multiple tubes with pre-set flow rates are attached either in-series or in parallel to allow the user to vary the flow rate of the therapy. The modular systems described herein may be used in connection with a constant pressure pump for subcutaneous administration of therapeutic agents.

28 Claims, 2 Drawing Sheets

(51) Int. Cl.
*A61M 39/08* (2006.01)
*A61M 39/28* (2006.01)
*A61M 25/00* (2006.01)
*A61M 5/145* (2006.01)
*A61M 5/162* (2006.01)

(52) U.S. Cl.
CPC .......... *A61M 25/002* (2013.01); *A61M 39/08* (2013.01); *A61M 39/28* (2013.01); *A61M 5/1456* (2013.01); *A61M 5/162* (2013.01); *A61M 5/16813* (2013.01); *A61M 2039/082* (2013.01)

(58) Field of Classification Search
CPC .. A61M 5/1413; A61M 39/28; A61M 39/287; A61M 5/16804; A61M 5/16877; A61M 5/16813
See application file for complete search history.

(56) References Cited

U.S. PATENT DOCUMENTS

| | | | | |
|---|---|---|---|---|
| 4,723,947 A * | 2/1988 | Konopka | ............ | A61M 39/08 156/294 |
| 4,863,429 A * | 9/1989 | Baldwin | ............ | A61M 5/1454 138/137 |
| 5,318,515 A * | 6/1994 | Wilk | .................... | A61M 5/141 604/186 |
| 5,356,379 A * | 10/1994 | Vaillancourt | ....... | A61M 5/1424 604/131 |
| 5,380,287 A * | 1/1995 | Kikuchi | .............. | A61M 5/1454 604/135 |
| 5,549,550 A * | 8/1996 | Mazer | .................. | A61M 5/007 604/8 |
| 5,840,058 A * | 11/1998 | Ammann | ............ | A61M 5/142 604/30 |
| 5,910,135 A * | 6/1999 | Hadzic | .................. | A61M 5/141 604/251 |
| 5,921,965 A * | 7/1999 | Blei | .................... | A61M 5/1408 138/118 |
| 5,927,326 A * | 7/1999 | Hiejima | ................ | A61M 5/141 137/599.11 |
| 6,095,491 A * | 8/2000 | Kriesel | ............ | A61M 5/16881 137/355 |
| 6,146,360 A * | 11/2000 | Rogers | .................. | A61M 5/148 604/151 |
| 6,645,183 B2 * | 11/2003 | Christensen | ...... | A61M 5/16804 604/244 |
| 66,696,683 * | 12/2003 | Kleeman | ............... | A61M 5/148 222/100 |
| 6,926,706 B1 * | 8/2005 | Sealfon | .................. | A61M 5/141 604/500 |
| 6,979,315 B2 * | 12/2005 | Rogers | ............. | A61M 5/14276 604/151 |
| 7,540,854 B2 * | 6/2009 | Trombley, III | ....... | A61M 5/142 600/431 |
| 2002/0107502 A1 * | 8/2002 | Hung | ................. | A61B 10/0045 604/506 |
| 2002/0115966 A1 * | 8/2002 | Christensen | ...... | A61M 5/16804 604/264 |
| 2002/0123741 A1 * | 9/2002 | Rake | ..................... | A61M 5/148 604/890.1 |
| 2003/0153867 A1 * | 8/2003 | Grifols | .................... | A61M 5/14 604/34 |
| 2006/0100578 A1 * | 5/2006 | Lieberman | ................ | A61J 1/05 604/132 |
| 2007/0173786 A1 * | 7/2007 | Recinella | .......... | A61M 25/0026 604/523 |
| 2010/0140288 A1 * | 6/2010 | Jones | .................. | B01F 15/0244 222/1 |
| 2011/0097229 A1 * | 4/2011 | Cauley, III | .......... | A61M 5/1454 417/518 |
| 2012/0259291 A1 * | 10/2012 | Lareau | ................... | A61M 39/22 604/247 |
| 2014/0039396 A1 * | 2/2014 | Geipel | ............. | A61M 5/14216 604/152 |
| 2014/0303559 A1 * | 10/2014 | Jung | ................... | A61M 5/1454 604/135 |
| 2016/0256625 A1 * | 9/2016 | Sealfon | ............... | A61M 5/1413 |

OTHER PUBLICATIONS

International Preliminary Report on Patentability for PCT/US2014/016426, dated Aug. 18, 2015.

* cited by examiner

MULTI-FLOW UNIVERSAL TUBING SET

CROSS-REFERENCE TO RELATED APPLICATIONS

This application is a National Stage of International Application No. PCT/US2014/016426, filed Feb. 14, 2014, which claims the benefit under 35 U.S.C. § 119(e) of U.S. Provisional Application no. 61/765,464, filed Feb. 15, 2013, the contents of all of which are incorporated herein in their entireties by reference thereto.

TECHNICAL FIELD

The subject matter disclosed herein relates to a modular tubing system for infusion systems.

BACKGROUND

Increasingly there is market demand to reduce the costs of providing intravenous and subcutaneous administrations. Programmable pumps that control the rate of flow of a therapy are effective but the cost may be prohibitive for many users. Constant-pressure pumps have been found to be safer and are more financially accessible to users, however, they lack some of the versatility of programmable flow rate control pumps. For a constant-pressure pump, when a certain flow rate is desired, the user may select tubing with an appropriate pre-set flow rate. The market offers a wide range of needle systems and different tubing sets. However, if a user would like to vary the flow rate, i.e., increase or decrease the flow rate, over the course of administration or over the course of use of a therapy, their options are limited.

One option the user has is to stop administering the therapy and replace the pre-set flow tubing with other tubing that provides a different flow rate. This solution may result in contamination and is susceptible to user error as the user removes and replaces the tubing with new tubing. In addition, the user is limited to the pre-set flow rate of the tubing and if a new flow rate is desired, the tubing would need to be switched yet again. For example, if a user desires to start administration with a slow infusion rate and gradually increase over the course of the administration, the pre-set flow-rate tubing would need to be switched out multiple times to achieve the user's needs.

The present methods of subcutaneous administration with pre-set flow tubing lack the versatility needed by users. A subcutaneous method of administration that is affordable and allows the user to vary the rate of administration with ease is needed.

SUMMARY OF THE INVENTION

In certain aspects, the invention provides a modular tubing system for delivering a therapeutic agent to a patient at a desired flow rate, comprising: a source containing a therapeutic agent; an outlet for delivering the therapeutic agent into the body of the patient; a plurality of tubing segments in fluid communication with the source and the outlet and aligned in a parallel relationship for simultaneously conducting the flow of therapeutic agent from the source to the outlet; and one or more flow-stopping means to stop the flow of therapeutic agent in one or more of the tubing segments. In certain embodiments, the flow-stopping means is a clamp such as a slide clamp.

The invention further provides a modular tubing system for delivering a therapeutic agent to a patient at a desired flow rate, comprising: a source containing a therapeutic agent; an outlet for delivering the therapeutic agent into the body of the patient; two or more tubing segments connected in-series through connectors wherein the connected segments conduct the flow of therapeutic agent from the source to the outlet. In certain embodiments, one or more of the tubing segments may be removed from the system and the remaining segments may be connected to restore the flow of therapeutic agent from the source to the outlet.

In certain embodiments, the source is a syringe. The outlet of the system may comprise one or more needles such as three needles. The plurality of tubing segments may be selected from between two and five tubing segments, such as between two and four segments. In particular embodiments, at least two of the tubing segments have different pre-set flow rates from each other.

The invention further comprises a kit comprising any modular tubing system disclosed herein, or portions thereof. Certain kits of the invention comprise a needle set comprising one or more needles; a modular tubing system for delivering a therapeutic fluid to the body of a patient at a desired flow rate, comprising: a plurality of tubing segments connected in a parallel relationship; and one or more flow-stopping means to stop the flow of therapeutic agent in one or more of the tubing segments. In certain embodiments, a kit of the invention comprises: a needle set comprising one or more needles; and a modular tubing system for delivering a therapeutic fluid to the body of a patient at a desired flow rate, comprising: a plurality of tubing segments connected in-series. In certain embodiments, the plurality of tubing segments in the kit is selected from between two and five tubing segments. In certain embodiments, at least two of the tubing segments have different pre-set flow rates from each other. The kits described herein may include instructions for using the modular tubing system for administering a therapeutic agent to a patient.

DESCRIPTION OF THE INVENTION

Figure 1:
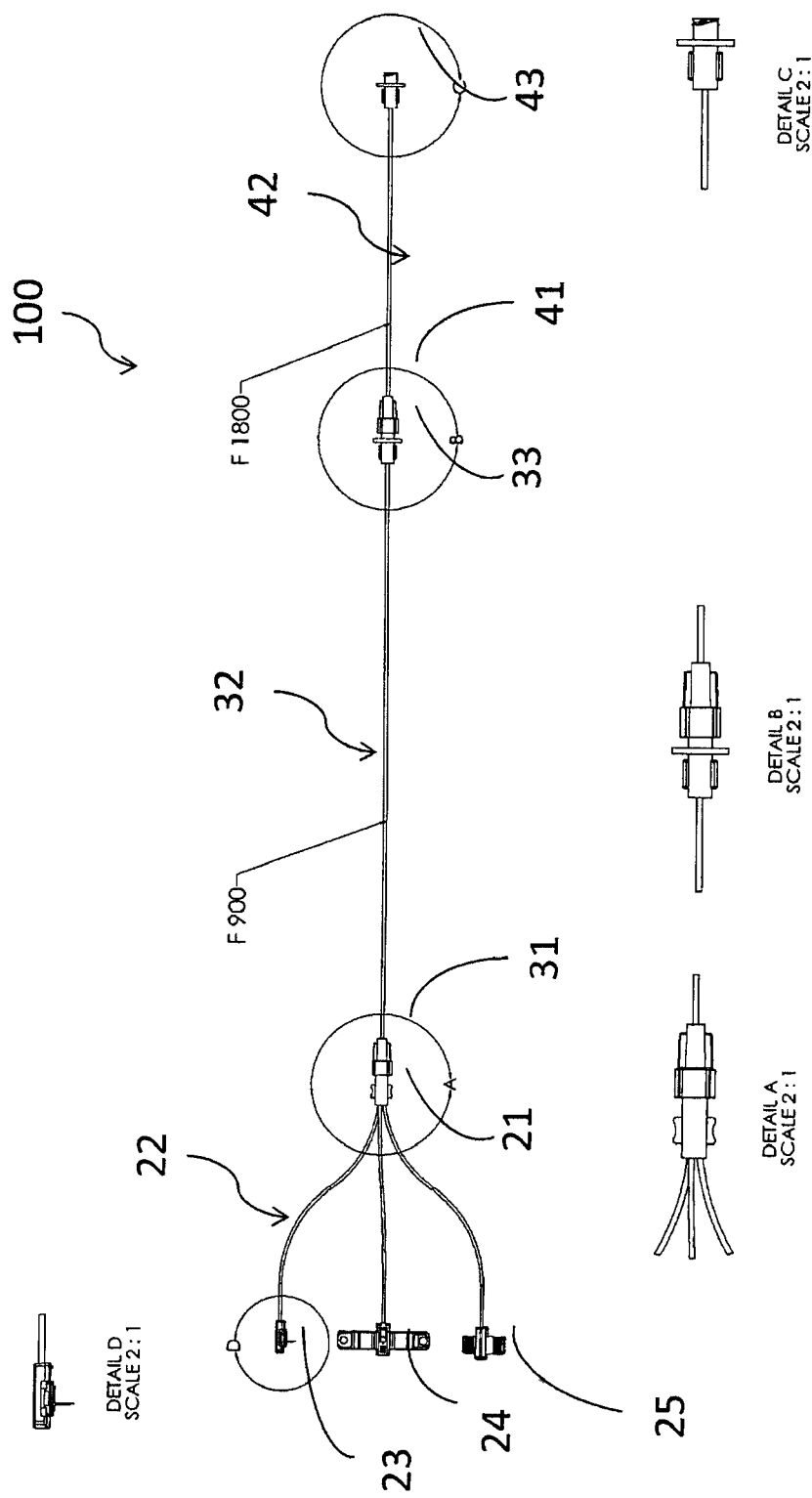
FIG. 1 depicts an exemplary configuration of the in-series modular tubing system. The outlet tri-needle set 22 is connected through connectors 21 and 31 to a tubing segment 32 which is connected in series to tubing segment 42. Tubing segment 42 is connected through connector 43 to a source such as a syringe in a syringe pump.

The invention provides modular tubing systems with a set of tubing segments that can be configured to provide a desired flow rate for infusion systems. In the modular systems described herein, a plurality of tubing segments with pre-set flow rates are attached either in-series or in parallel to allow the user to vary the flow rate of the therapy. In preferred embodiments, the modular systems described herein are used in connection with a constant-pressure pump.

Tubing segments may be selected with different pre-set flow rates in order to achieve a final desired rate of infusion to the patient. The pre-set flow rates are generally controlled by the internal diameter of the tubing. For example, tubing with a large internal diameter has a higher pre-set flow rate than tubing with a narrower diameter. The pre-set flow rates determined by the manufacturer of a tubing segment need not correlate with the actual rate of flow used to deliver a therapeutic agent due to the viscosity of the fluid and/or the pressure applied by the pump. For example, a tubing segment may permit a flow rate of water of up to 900 mL/hour based upon its internal diameter and length but a constant-pressure pump delivers a viscous agent through the tube at a far slower rate, e.g., 60 mL/hour. In some embodiments, at least two of the tubing segments of a modular tubing system have different pre-set flow rates from each other, e.g., different internal diameters. In other embodiments, each of the tubing segments of a modular tubing system have the same pre-set flow rates. Tubing segments suitable for the systems of the invention include, for example, RMS Medical Products tubing: F30, F45, F60, F120, F180, F420, F600, F900, F1200, and F2400.

The systems described herein may be used in the administration of a therapy to a patient. In particular, the systems may be used for infusion therapy to a patient such as subcutaneous or intravenous infusion therapy. The therapy may be selected from any therapeutic agent or combination of therapeutic agents administered through infusion therapy. Therapeutic agent as used herein refers to one or more therapeutic agents optionally formulated for administration to a patient. In particular embodiments, the therapeutic agent is a biologic agent such as an immunoglobulin.

In certain embodiments, the user of the systems described herein is the patient receiving the therapy. In other embodiments, the user of the system is a person other than the patient such as a health care provider.

The modular tubing systems described herein are preferably used with constant-pressure pumps. Constant-pressure pumps apply a constant pressure to suppress the barrel of a syringe containing the therapeutic agent. The therapeutic agent is released from the source, i.e., the syringe, into the modular tubing which serves to control the flow rate delivered though the outlet to the patient, as further described herein. One example of a constant-pressure pump is the Freedom60® infusion system from RMS Medical Products. In certain aspects, the constant-pressure pump, such as the Freedom60® infusion system, adjusts to patient saturation. That is, if the flow is too fast into the patient's sites, the increasing back pressure will serve to slow the delivery rate down and insure that excess flow rate does not occur.

The modular system may include one or more outlet needles. In certain embodiments, each needle is capable of delivering a therapeutic agent to the site at up to 25 mL or more of a therapeutic agent at one dosing. For a modular system with multiple needles, patients who do not desire to use all the needles can block off one or more of the needles using a slide clamp. For the delivery of the therapeutic agent Hizentra, for example, a 50 mL dose could be delivered with only two needles according to the package insert, but many patients may experience substantially reduced site reactions if three needles are used for administration.

Series Configuration:

For the in-series system, two or more tubing segments are attached in-series in order to allow the user to control the flow rate. If the user desires a change in flow rate, one or more of the tubing segments may be removed. For example, a first tubing segment with a pre-set flow rate of 900 mL/hour and a second tubing segment with a pre-set flow rate of 1800 mL/hour are connected in-series through, for example, a connector such as a luer connector. The connected tubing segments are used as a conduit to deliver the therapy from the source, e.g., syringe in a syringe pump, to the outlet, e.g., one or more needles subcutaneously placed in a patient.

If the user desires a change in flow rate, one or more of the tubes may be removed. For example, at the beginning of an administration, two tubing segments serve as a conduit between the source and the outlet and the tubing segments have pre-set flow rates of 900 mL/hour and 1800 mL/hour respectively. If the user then desires to increase the flow rate of the administration, one of the tubing segments may be removed, e.g., in the exemplary system either the 900 mL/hour segment or the 1800 mL/hour segment is removed. Once a tubing segment is removed, either the outlet or the source is reconnected to the remaining tubing segment, depending on which of the tubing segments was removed, and the user may resume administration at an increased rate of flow.

To further illustrate, FIG. 1 depicts an embodiment of the in-series system. In FIG. 1, a modular in-series system 100, has an outlet comprising a tri-needle set 22 including needles 23-25. The outlet tri-needle set 22 is connected through connectors 21 and 31 to a tubing segment 32. Tube 32 has a first connector 31 at one end, and a second connector 33 at the other end. Similarly, tube 42 has a first connector 41 at one end, and a second connector 43 at the other end. Tubing segment 32 is connected in-series through connector 33 and 41 to tubing segment 42. Tubular segment 42 is connected through connector 43 to a source such as a syringe in a syringe pump. In certain embodiments, tubes 32 and 42 have the same pre-set flow rate. In some embodiments, tubes 32 and 42 have different pre-set flow rates. In some embodiments, one or more connectors 21, 31, 33, 41, and 43 are luer connectors. In preferred embodiments, the syringe pump is a constant-pressure pump.

In certain embodiments, the needles of the tri-needle set 22 are inserted subcutaneously into the patient and the therapy is administered though the in-series system 100. Over the course of the administration, if the user decides to increase the rate of administration, the user may remove one of tubing segments 32 or 42. Once a tubing segment is removed, the system may be reconnected and administration continued. For example, if tubing segment 32 is removed via connectors 31 and 33, connector 41 may be connected to connector 21 and the administration may be resumed. If tubing segment 42 is removed via connectors 41 and 43, connector 33 may be connected to the source, e.g., a syringe, and the administration may be resumed. The result is that the exemplary in-series system may provide the user with the option of three different flow rates: slow, e.g., when both tubing segments are used, medium, e.g., when a slower one of the two tuning segments is used, and fast, e.g., when a faster one of the two tubing segments is used.

The outlet of the system may vary as to the needs of the user and may include, for example, one or more needles. If the outlet comprises multiple needles, the multiple needles may be the same or different such as needles with different lengths for varying areas of the body. In one embodiment, three 9-10 mm needles may be used in the outlet for patients receiving up to 75 mL of a therapy such as Hizentra.

To illustrate an exemplary use of the in-series system of the invention, Table 1 displays the administration time for 50 mL and 60 mL of Hizentra, an immunoglobulin therapy. Table 1 shows the different flow rates that can be achieved using the modular system 100 of FIG. 1 for the administration for Hizentra. For example, one can administer the therapy with a system that includes two tubing segments connected in-series, where one tubing segment 32 is F900, and a second tubing segment 42 is F1800, and the resulting flow rate is equivalent to that of F600 tubing. If an equivalent F900 is desired, then the F1800 tubing 42 can be removed and discarded. If the F1800 is desired, the F900 tubing 32 can be removed, and the F1800 tubing 42 can be connected directly to the needle set 22.

TABLE 1

Administration of Hizentra using in-series tubing segments to control flow rate

| Typical Example of multiflow trifurcated needle set 2 in series | Works as | Delivers 50 ml Hizentra | Delivers 60 ml Hizentra |
|---|---|---|---|
| As Delivered | F600 | 1:28 | 1:46 |
| F900 alone | F900 | 1:07 | 1:21 |
| F1800 alone | F1800 | :46 | :56 |

In some embodiments, a set of three tubing segments connected in series can be provided to achieve a desired range of flow rates. In some embodiments, four or more tubing segments can be provided. The equivalent flow rate ($F_{eq}$) of N number of tubes connected in-series can be calculated as follow:

$$\frac{1}{F_{eq}} = \frac{1}{F_1} + \frac{1}{F_2} + \frac{1}{F_3} + \ldots + \frac{1}{F_N}$$

The in-series and parallel tubing sets described herein may be used in combination to achieve a greater variety of flow rates. In certain embodiments, one or more in-series tubing sets is used in connection with one or more parallel tubing sets. For example, a parallel tubing set may be connected on one end to a source and on the other end to an in-series tubing set through a connector. The end of the in-series tubing set not connected to the parallel tubing set may then be connected to an outlet such as one or more needles. To achieve different flow rates, one or more of the parallel tubing segments may be closed with a flow stopping means and/or one or more of the in-series tubing segments may be removed. By combining the in-series and parallel tubing sets, multiple flow rates may be achieved.

Parallel Configuration:

In another aspect, the invention provides a modular system of tubing segments connected in parallel. For the parallel system, two or more tubing segments are attached in parallel in order to allow the user to control the flow rate. If the user desires a change in flow rate, one or more of the tubing segments may be closed to stop the flow through that tubing segment. For example, a first tubing segment with a pre-set flow rate of 300 mL/hour and a second tubing segment with a pre-set flow rate of 600 mL/hour are connected in parallel, e.g., with "Y" connectors at both ends of the tubes, and each of the separate tubing segments may be individually closed off with, for example, a clamp, to prevent flow through the closed off tubing segment. The tubing segments are used as conduits to deliver the therapy from the source, e.g., syringe in a syringe pump, to the outlet, e.g., one or more needles subcutaneously placed in a patient.

Multiple flow rates can also be achieved using the parallel tubing segments. For example, both tubes may be open, i.e., not closed off, allowing the therapeutic agent to travel from the source to the outlet through both of the parallel tubes. Alternatively only one of the tubes is open at a time and the other tube is closed off. A tubing segment may be closed off by any means known in the art for closing the flow of a substance through a tube. For example, a tubing segment may be closed off with a clamp such as a slide clamp, a switching block, a pinch connector or a valve in the tubing segment. The tubing segment may be closed off by physical manipulation such as by bending the tube in half or squeezing the tube to prevent flow through the tubing segment. An example of three different flow rates that can be achieved using a parallel two-tubing segment system may be seen in Table 2.

TABLE 2

Administration of Hizentra using two parallel tubing segments to control flow rate

| Two tubing segments in parallel (F1200 and F600) | F1200 status | F600 status | Equivalent F ($F_{eq}$) | Delivery time of 50 mL Hizentra | Delivery time of 60 mL Hizentra |
|---|---|---|---|---|---|
| Slow | closed | open | F600 | 1 hour 28 minutes | 1 hour 46 minutes |
| Medium | open | closed | F1200 | 57 minutes | 1 hour 8 minutes |
| Fast | open | open | F1800 | 46 minutes | 56 minutes |

Figure 2:
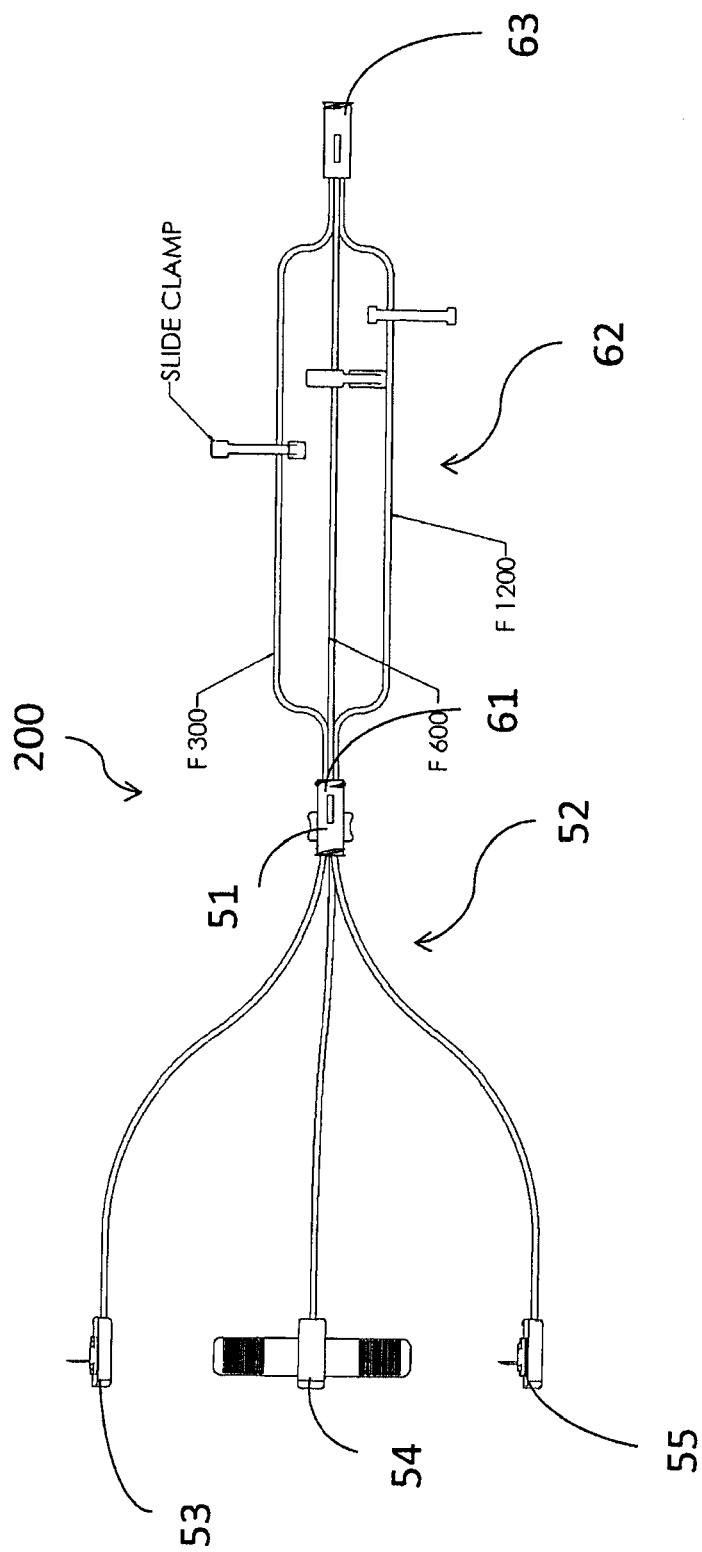
FIG. 2 depicts an exemplary configuration of the parallel modular tubing system. The outlet tri-needle set 52 is connected through connectors 51 and 61 to tri-parallel tubing segment 62. The tri-parallel-tubing set 62 is connected through connector 63 to a source, such as a syringe or one or more tubing segments to be connected in-series.

To further illustrate, FIG. 2 shows an exemplary parallel-tubing modular system 200. Modular system 200 includes an outlet comprising a tri-needle set 52 connected to a tri-parallel-tubing set 62, i.e., three tubing segments connected in parallel to each other. The tri-needle set 52 includes connector 51 at one end for connecting to connector 61 of the tri-parallel-tubing set 62. At the opposite end, the tri-parallel-tubing set 62 is connected through connector 63 for connection to a source, e.g., a syringe or one or more tubing segments to be connected in-series. The tri-parallel-tubing set 63 includes three tubing segments that are connected in parallel: F300, F600, and F1200. Seven different flow rates, excluding the option when all three tubes are closed and no flow is permitted, can be obtained as can be seen in Table 3.

TABLE 3

Administration of Hizentra using three parallel tubing segments to control flow rate

| | F300 status | F600 status | F1200 status | Equivalent F ($F_{eq}$) | Delivery time of 50 mL Hizentra | Delivery time of 60 mL Hizentra |
|---|---|---|---|---|---|---|
| 1 | open | closed | closed | 300 | 2 hours 31 minutes | 3 hours 1 minute |
| 2 | closed | open | closed | 600 | 1 hour 28 minutes | 1 hour 46 minutes |
| 3 | open | open | closed | 900 | 1 hour 7 minutes | 1 hour 21 minutes |
| 4 | closed | closed | open | 1200 | 57 minutes | 1 hour 8 minutes |
| 5 | open | closed | open | 1500 | 50 minutes | 1 hour 1 minute |
| 6 | closed | open | open | 1800 | 46 minutes | 56 minutes |
| 7 | open | open | open | 2100 | 43 minutes | 52 minutes |

Additional tubing segments in parallel, such as four, five or six tubes in parallel, may be used to achieve any number of flow rates as desired. When N number of tubes having F numbers of $F_1, F_2, F_3 \ldots F_N$ are connected in parallel, the resulting equivalent F number ($F_{eq}$) can be calculated as follows:

$$F_{eq} = F_1 + F_2 + F_3 + \ldots + F_N$$

A parallel tubing set may be used in combination with one or more other tubing sets such as one or more tubing sets selected from in-series tubing sets and parallel tubing sets. For example, two parallel tubing sets may be connected to each other in series to provide the possibility of additional flow rate options.

Kits:

The invention further provides kits comprising any of the modular systems described herein, or portions thereof, for delivering therapeutic agents. In certain embodiments, kits of the invention comprise a needle set comprising one or more needles and a modular tubing system for delivering a therapeutic agent to a patient at a desired flow rate. The modular system may comprise a plurality of tubing segments connected in a parallel relationship and one or more flow stopping means to stop the flow of therapeutic agent in one or more of the tubing segments.

The modular system may comprise a plurality of tubing segments connected in-series. The plurality of tubing segments may be selected from between two and five tubing segments such as between two and four tubing segments. In certain embodiments, at least two of the tubing segments have different pre-set flow rates from each other. In certain embodiments, the plurality of tubing segments is three or more tubing segments. In certain embodiments, at least three of the tubing segments have different pre-set flow rates from each other. In some embodiments, the kit can also include a needle set including one or more needles connected in parallel to one another for connection to one or more in-series tubing segments and/or parallel tubing segment sets. The kit may further include instructions for using the modular tubing system.

In certain embodiments, the kit of the invention comprises an plurality of tubing segments connected in-series (in-series tubing set) or a plurality of tubing segments connected in a parallel relationship (in-parallel tubing set). The tubing sets may be pre-assembled in the kit or may require assembly by the user. In preferred embodiments, the tubing set comes pre-assembled in the kit.

In particular embodiments, the kit includes an in-series tubing set and the tubing segments connected in-series may have different pre-set flow rates from each other or the same pre-set flow rates. In preferred embodiments, the in-series tubing set has two tubing segments with different pre-set flow rates from each other connected in-series. The tubing set may contain one or more connectors connecting the tubing segments in-series. The tubing set may also include one or more connectors to connect the tubing set to an outlet or source.

In particular embodiments, the kit includes an in-parallel tubing set and the tubing segments connected in-parallel may have different pre-set flow rates from each other or the same pre-set flow rates. In preferred embodiments, the parallel tubing set has two tubing segments with different pre-set flow rates connected in parallel. The tubing set may contain one or more connectors connecting the tubing segments in-parallel. The tubing set may also include one or more connectors to connect the tubing set to an outlet or source.

The kits with in-series or parallel tubing sets described herein may also comprise one or more of the following components:

1) a needle
2) a needle set with two or more needles;
3) an in-series tubing set;
4) a parallel tubing set;
5) a syringe;
6) one or more connectors such as luer or Y connectors;
7) a stopper, clamp or valve;
8) instructions for using the in-series or parallel tubing sets;
9) instructions for assembling the in-series of parallel tubing sets;
10) instructions for connecting the in-series or parallel tubing sets to the source or the outlet.

In certain embodiments, the kit comprises a plurality of tubing sets such as one or more in-series tubing sets and one or more parallel tubing sets. For example, the kit may comprise one parallel tubing set and one in-series tubing set. The tubing sets may be pre-connected to each other in the kit or may require assembly by the user.

An in-series or parallel tubing set may be connected to one or more other components in the kit or the in-series or parallel tubing set may be free standing from other components in the kit. For example, a kit may comprise an in-series tubing set and a needle set wherein the needle set and in-series tubing are not connected in the kit. The user may connect the in-series tubing set and needle set with one or more connectors. Alternatively, the kit may comprise an in-series tubing set and a needle set wherein the needle set and in-series tubing are connected in the kit with one or more connectors.

In addition, when a kit contains two or more components in addition to the in-series or parallel tubing set, the two or more additional components may be connected or free standing from each other. For example, a kit may comprise the additional components of a needle set and a clamp. The clamp may be clamped onto a portion of the needle set or the clamp may be free standing from the needle set. The present invention provides among other things systems for administering therapeutic agents to patients and kits thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

What is claimed is:

1. A modular flow control tubing system for delivering a therapeutic agent to a patient at a controlled and variable flow rate, comprising:
a source containing a therapeutic agent to be dispensed by a fluid pump;
an outlet for delivering the therapeutic agent into the body of the patient;
a plurality of flexible tubing segments in fluid communication with the source and the outlet, each tubing segment having a length from a proximal end to a distal end and a known pre-set flow rate generally established by a consistent internal diameter along the length to create a known flow rate for the therapeutic agent passing therethrough, the tubing segments aligned in a parallel relationship with the proximal ends joined to a connector for coupling to the source for simultaneously conducting the flow of therapeutic agent at a second known flow rate from the source to the outlet, the second known flow rate established by the known pre-set flow rates of each tubing segment permitting parallel flow, during use the tubing segments unenclosed such that they are exposed along their lengths; and one or more flow-stopping means to stop the flow of therapeutic agent in one or more of the plurality of tubing segments;

wherein a user may selectively engage one or more flow stopping means to the plurality of tubing segments to establish a known flow rate of the therapeutic agent from the fluid pump into the patient.

2. The modular tubing system according to claim 1, wherein at least one of the one or more flow-stopping means is a clamp.

3. The modular tubing system according to claim 2, wherein the clamp is a slide clamp.

4. The modular tubing system according to claim 1, wherein the source is a syringe.

5. The modular tubing system according to claim 1, wherein the plurality of tubing segments is selected from between two and five tubing segments.

6. The modular tubing system according to claim 5, wherein at least two of the plurality of tubing segments have different pre-set flow rates.

7. The modular tubing system according to claim 1, wherein the outlet comprises one or more needles.

8. A kit comprising a modular tubing system of claim 1.

9. The modular tubing system according to claim 1, wherein the fluid pump is a constant force fluid pump.

10. A modular flow control tubing system for delivering a therapeutic agent to a patient at a controlled and variable flow rate, comprising:

a source containing a therapeutic agent to be dispensed by a fluid pump;

an outlet for delivering the therapeutic agent into the body of the patient;

a plurality of unconnected, flexible tubing segments each configured as a free standing element and unconnected prior to selection and interconnection assembly by a user prior to use, each having a length from a proximal end having a first connector to a distal end having a second connector and a known pre-set flow rate generally established by a consistent internal diameter along the length to create a known flow rate for the therapeutic agent passing therethrough, two or more unconnected tubing segments to be directly connected in series through the connectors as a flow rate controlled pathway from the source to the outlet, wherein the selection and connection of at least a subset of tubing segments establishes an overall known flow rate of the therapeutic agent from the fluid pump through the flow rate controlled pathway to the patient the overall known flow rate established by the known pre-set flow rates of each tubing segment comprising the flow rate controlled pathway.

11. The modular tubing system of claim 10, wherein one or more of the tubing segments may be removed from the modular tubing system and the remaining segments may be connected to restore the flow of therapeutic agent from the source to the outlet at a different known flow rate.

12. The modular tubing system according to claim 10, wherein at least a subset of the unconnected tubing segments includes: at least a first tubing segment having a known first pre-set flow rate, a second tubing segment having a known second pre-set flow rate, and a third tubing segment having a known third pre-set flow rate—collectively the unconnected tubing segment set, wherein engaging in series at least two tubing segments selected from the unconnected tubing segment set provides a combined tubing pathway with a known pre-set flow rate that is less than the known pre-set flow rate of each engaged tubing segment, the tubing segment set providing a range of overall known pre-set flow rates.

13. The modular tubing system according to claim 10, wherein the source is a syringe.

14. The modular tubing system according to claim 10, wherein the plurality of unconnected tubing segments is selected from between two and five unconnected tubing segments.

15. The modular tubing system according to claim 10, wherein at least two of the plurality of unconnected tubing segments have different pre-set flow rates.

16. The modular tubing system according to claim 10, wherein the fluid pump is a constant force fluid pump.

17. A kit for delivering a therapeutic agent to a patient at a controlled and variable flow rate, the kit comprising:

a needle set comprising one or more needles; and a modular tubing system for delivering a therapeutic fluid to the body of a patient at a known flow rate, comprising:

a plurality of unconnected, flexible tubing segments at least a subset configured as free standing elements and unconnected prior to selection and interconnection assembly by a user prior to use, each having a length from a proximal end to a distal end and a known pre-set flow rate generally established by a consistent internal diameter along the length to create a known flow rate for the therapeutic agent passing therethrough, at least two tubing segments having different pre-set flow rates, two or more unconnected tubing segments to be selected and engaged with each other to provide a flow rate controlled pathway with an overall known flow rate different from the pre-set flow rate of each engaged tubing segment to conduct a flow of the therapeutic agent from a therapeutic agent source to the outlet at the known flow rate, the overall known flow rate established by the known pre-set flow rates of each tubing segment comprising the flow rate controlled pathway.

18. The kit according to claim 17, wherein the plurality of tubing segments is selected from between two and five tubing segments.

19. The kit according to claim 17, wherein at least two of the plurality of tubing segments are engaged in parallel as parallel segments, and at least one tubing segment is engaged in series with and following the parallel segments, as the flow rate controlled pathway from the therapeutic agent source to the patient.

20. The kit according to claim 17, further comprising one or more flow-stopping means to stop the flow of therapeutic agent in one or more of the selected tubing segments engaged to be connected in parallel.

21. A modular flow control tubing system for delivering a therapeutic agent to a patient at a controlled and known pre-selected flowrate, comprising:

an inlet for connection to a source containing a therapeutic agent to be dispensed by a fluid pump;

an outlet for delivering the therapeutic agent into the body of the patient;

a plurality of unconnected, flexible tubing segments at least a subset configured as free standing elements and unconnected prior to selection and interconnection assembly by a user prior to use, each having a length from a proximal end to a distal end and a known pre-set flow rate generally established by a consistent internal diameter along the length to create a known flow rate for the therapeutic agent passing therethrough, at least two tubing segments having different pre-set flow rates, two or more unconnected tubing segments to be engaged with each other to provide a combined tubing segment with an overall known flow rate different from the pre-set flow rate of each engaged tubing segment to conduct a flow of the therapeutic agent directly from the source to the outlet at the known flow rate, the overall known flow rate established by the flow rates of each tubing segment comprising the combined tubing segment.

22. The modular tubing system according to claim 21, wherein the source is a syringe.

23. The modular tubing system according to claim 21, wherein the fluid pump is a constant force fluid pump.

24. The modular tubing system according to claim 21, wherein the plurality of unconnected tubing segments is selected from between two and five unconnected tubing segments.

25. The modular tubing system according to claim 21, wherein at least two of the tubing segments engaged are connected in parallel.

26. The modular tubing system according to claim 21, wherein at least two of the tubing segments engaged are connected in series.

27. The modular tubing system according to claim 21, wherein at least a subset of the unconnected tubing segments includes: at least a first tubing segment having a known first pre-set flow rate, a second tubing segment having a known second pre-set flow rate, and a third tubing segment having a known third pre-set flow rate—collectively the unconnected tubing segment set, wherein engaging in series at least two tubing segments selected from the unconnected tubing segment set provides a combined tubing pathway with a known pre-set flow rate that is less than the known pre-set flow rate of each engaged tubing segment, the tubing segment set providing a range of overall known pre-set flow rates.

28. The modular tubing system according to claim 21, wherein at least two of the plurality of tubing segments are engaged in parallel as parallel segments, and at least one tubing segment is engaged in series with and following the parallel segments, as the flow rate controlled pathway from the therapeutic agent source to the patient.

* * * * *